US010549269B2

United States Patent
Schaadt et al.

(10) Patent No.: US 10,549,269 B2
(45) Date of Patent: Feb. 4, 2020

(54) CATALYST COMPRISING FLUORINATED METAL OXIDE, MANUFACTURE PROCESS AND HYDROGENATION PROCESS

(71) Applicants: Fraunhofer-Gesellschaft zur Förderung der angewandten Forschung e.V., Munich (DE); Solvay SA, Brussels (BE); Albert-Ludwigs-Universität Freiburg, Freiburg (DE)

(72) Inventors: Achim Schaadt, Freiburg (DE); Ingo Krossing, Freiburg (DE); Mathias Feinäugle, Freiburg (DE); Valentin Dybbert, Freiburg (DE); Harald Hillebrecht, Freiburg (DE); Thilo Ludwig, Freiburg (DE); Johannes Eicher, Sehnde (DE); Elias Frei, Berlin (DE)

(73) Assignees: Fraunhofer-Gesellschaft zur Förderung der angewandten Forschung e.V. (DE); SOLVAY SA (BE); Albert-Ludwigs-Universität Freiburg (DE)

(*) Notice: Subject to any disclaimer, the term of this patent is extended or adjusted under 35 U.S.C. 154(b) by 0 days.

(21) Appl. No.: 15/494,176

(22) Filed: Apr. 21, 2017

(65) Prior Publication Data

US 2017/0216830 A1      Aug. 3, 2017

Related U.S. Application Data

(63) Continuation of application No. PCT/EP2015/075309, filed on Oct. 30, 2015.

(30) Foreign Application Priority Data

Oct. 31, 2014  (EP) .................................... 14191287

(51) Int. Cl.
| | |
|---|---|
| *B01J 37/26* | (2006.01) |
| *B01J 27/138* | (2006.01) |
| *C07C 29/153* | (2006.01) |
| *C07C 29/154* | (2006.01) |
| *C07C 41/01* | (2006.01) |

(52) U.S. Cl.
CPC ............. *B01J 37/26* (2013.01); *B01J 27/138* (2013.01); *C07C 29/153* (2013.01); *C07C 29/154* (2013.01); *C07C 41/01* (2013.01)

(58) Field of Classification Search
CPC ...... B01J 37/26; B01J 27/138; B01J 2523/00; B01J 27/12; B01J 2523/17; B01J 2523/27; B01J 2523/48; C07C 41/01; C07C 29/153; C07C 29/154; C07C 31/04
See application file for complete search history.

(56) References Cited

U.S. PATENT DOCUMENTS

| | | | |
|---|---|---|---|
| 1,681,751 A | 8/1928 | Storch | |
| 2,534,018 A | 12/1950 | Gresham et al. | |
| 2,744,148 A | 5/1956 | Ruh et al. | |
| 4,275,046 A | 6/1981 | McVicker et al. | |
| 6,281,277 B1* | 8/2001 | Ishii ...................... | B82Y 30/00 423/111 |

FOREIGN PATENT DOCUMENTS

| | | |
|---|---|---|
| CN | 103721719 A | 4/2014 |
| DE | 694 06 525 T2 | 5/1998 |
| EP | 1 232 791 A1 | 8/2002 |
| EP | 1 666 411 A1 | 6/2006 |
| WO | WO 2007/019359 A1 | 2/2007 |
| WO | WO 2007/149660 A1 | 12/2007 |

OTHER PUBLICATIONS

Zhao Ning et al., Catalyst for synthesizing methanol through carbon dioxide hydrogenation, CN 10372179, machine translation, Apr. 16, 2014.*
International Search Report, dated Feb. 22, 2016, pp. 1-4, issued in International Patent Application No. PCT/EP2015/075309, European Patent Office, Rijswijk, The Netherlands.

* cited by examiner

*Primary Examiner* — Jafar F Parsa
(74) *Attorney, Agent, or Firm* — Brinks Gilson & Lione

(57) ABSTRACT

A process for the manufacture of a catalyst comprising a fluorinated metal oxide is provided. A catalyst comprising a fluorinated metal oxide is provided. A catalytic hydrogenation process is also provided.

8 Claims, No Drawings

CATALYST COMPRISING FLUORINATED METAL OXIDE, MANUFACTURE PROCESS AND HYDROGENATION PROCESS

The present invention concerns a process for the manufacture of a catalyst, in particular a hydrogenation catalyst, comprising a fluorinated metal oxide. The invention further concerns a catalyst comprising a fluorinated metal oxide, and a catalytic hydrogenation process.

Catalytic processes, such as catalytic hydrogenation processes, have great importance in industry. The catalytic hydrogenation of the CO2, which is a waste gas contributing to the greenhouse effect, is of particular interest as CO2 content in the atmosphere can be reduced and concurrent obtention of new raw materials and fuels can be achieved, such as obtention of methanol, methane and dimethyl ether. Hydrogenation catalysts currently used are often restricted in their characteristics, such as activity, selectivity and lifetime of the catalyst. Therefore, there is an ongoing need for improved hydrogenation catalysts which show enhanced activity, selectivity and lifetime for certain hydrogenation processes, in particular in the hydrogenation of CO2.

CN103721719 discloses a carbon dioxide hydrogenation catalyst for methanol synthesis, wherein the catalyst contains Cu, Zn, Al, X, halogen and oxygen, X being a trivalent and/or tetravalent metal ion, wherein the halogen is introduced to the catalytic system by treatment of a catalyst precursor with an aqueous solution of NaF.

It was found, surprisingly, that a hydrogenation catalyst comprising a fluorinated metal oxide, obtained by fluorinating a catalyst precursor comprising a metal oxide with at least one gaseous fluorination agent, displays improved catalytic activity in particular in hydrogenation reactions.

The present invention consequently concerns a process for the manufacture of a catalyst, in particular a hydrogenation catalyst, comprising a fluorinated metal oxide, wherein the catalyst is manufactured by fluorination of a catalyst precursor comprising a metal oxide with at least one gaseous fluorinating agent. The invention further concerns a catalyst, in particular a hydrogenation catalyst, comprising a fluorinated ternary metal oxide, which is obtained by a process comprising the step of fluorination of a catalyst precursor comprising a metal oxide with at least one gaseous fluorinating agent.

The invention also concerns a process for catalytic hydrogenation, in particular the catalytic hydrogenation of CO2, wherein at least one hydrogenation catalyst is a catalyst comprising a fluorinated metal oxide, wherein the fluorinated metal oxide was obtained by fluorination of a catalyst precursor comprising a metal oxide with at least one gaseous fluorination agent.

The catalyst according to the present invention has improved properties particularly in the catalytic hydrogenation of CO2 and/or CO to methanol, but can also be suited as catalyst in other hydrogenation processes. Notably, the catalyst has an improved selectivity and activity in the conversion of CO2 to methanol at comparably low pressures, which is favorable for the economic viability of the process.

The term "catalyst" is intended to denote a substance that increases the rate of a reaction without modifying the overall standard Gibbs energy change in the reaction. Further, the catalyst can positively influence the selectivity of a reaction, and can allow for lower pressures and/or temperatures during the catalyzed reaction. The catalyst according to the present invention preferably is a hydrogenation catalyst. A hydrogenation generally is a chemical reaction between molecular hydrogen H2 and another compound or element. One example for a hydrogenation reaction which can be catalyzed with the catalyst according to the present invention, is the hydrogenation of unsaturated bonds to form saturated bonds, such as the partial or complete conversion of unsaturated fatty acids to partially or completely saturated fatty acids, and other partial or complete conversions from alkenes/aromatics to alkanes. Other hydrogenation processes which can be catalyzed by a catalyst according to the present invention include, for example, conversion of aldehydes to primary alcohols, ketones to secondary alcohols, esters to alcohols, imines to amines, amides to amines, nitriles to amines and nitro-groups to amine-groups. A most preferred catalytic hydrogenation process, which can be catalyzed by a hydrogenation catalyst according to the present invention, is the conversion of CO2 and/or CO to chemicals or fuels, notably methanol and/or dimethyl ether (DME). The conversion of CO2 and/or CO to methanol and/or DME is a preferred hydrogenation process which can be catalyzed by the catalysts according to the present invention. The general concept of catalytic hydrogenation conversion of CO2 and CO to methanol and/or DME is described in G. A. Olah et al, J. Org. Chem. 2009, 74, 487-498, which is hereby incorporated by reference.

The catalyst, in particular hydrogenation catalyst, of the present invention is a catalyst comprising a fluorinated metal oxide. The catalyst is prepared by fluorination of a catalyst precursor comprising a metal oxide with at least one gaseous fluorination agent. It has been found that the catalyst comprising a fluorinated metal oxide, wherein at least one gaseous fluorination agent was employed for the fluorination of the catalyst precursor, surprisingly displays improved properties with respect to the activity, selectivity and lifetime of the catalyst when compared to a catalyst comprising a metal oxide which was not fluorinated in the gas phase. This is in particular observed when the catalyst is employed in a catalytic hydrogenation process. For example, higher methanol selectivity at lower pressure and temperature has been observed in the conversion of CO2 in a catalytic hydrogenation. The catalyst according to the present invention also shows a higher CO2 turnover and a greater catalyst activity when compared to a catalyst comprising a metal oxide which was not fluorinated in the gas phase. The fluorination of a catalyst precursor comprising a metal oxide with at least one gaseous fluorination agent is a facile process, wherein the precursor is simply contacted with the at least one gaseous fluorination agent. Further workup steps, such as washing and drying as would be necessary when an aqueous fluorination agent would be used, are not needed.

The catalyst, in particular hydrogenation catalyst, according to the present invention is suitably obtained by a process comprising the step of fluorination of a catalyst precursor which comprises a metal oxide with at least one gaseous fluorination agent. The catalyst precursor often contains more than one, preferably two, three or four different metals. The term "metal" intends to denote a metal atom species bearing all kinds of oxidation states suitable for the individual atom species. Generally, the catalyst precursor and the hydrogenation catalyst can contain metal atoms in the oxidation state 0 as well as metals in the oxidation state that will balance the anions contained in the structure, in particular oxidic or oxidofluoridic structure, and suitable for the metal atom species. The catalyst precursor often comprises a metal oxide, preferably containing more than one metal atom species, as main component. Yet, in another aspect other components can also be present, such as metal hydroxides and/or metal carbonates and hydrates of the foregoing, or other metal salts. A catalyst precursor containing a metal oxide containing one or more, preferably three or more, metal atoms, as only or substantially only component, is preferred. If the metal oxide contains more than one metal species, it is also referred to "mixed metal oxide". Often, if the oxide is a mixed oxide, the metals contained in the mixed oxide are all different from the other metals contained in the oxide. In another aspect, at least two metals are the same, but present in different oxidation states. Suitable metals according to the present invention are metals of group 3 to 14 or the series of lanthanoids, preferably group 3, 11, 12, 13 or 58 of the periodic system as determined by IUPAC Nomenclature (Handbook of Chemistry and Physic, 80th Edition, 1999-2000). Preferred metal oxides according to the present invention are ternary oxides. "Ternary oxides" intend to denote oxides which contain three different metal species M1, M2 and M3. In another aspect, the catalyst precursor comprises a quaternary metal oxide, which intends to denote oxides which contain four different metal species M1, M2, M3 and M4. Generally, the metals contained in the metal oxides are metals of group 3 to 14, preferably group 3, 11, 12 or 13, of the periodic system. In the present invention, the term "metal oxide" also denotes "metal oxides" and "mixed oxide or oxides".

In one embodiment, M1 is selected from group 11 or 12 of the periodic system, wherein M1 is most preferably Cu. In one preferred aspect, a ternary metal oxide contains M1=Cu, M2=Zn and M3=Zr. In another aspect, a ternary metal oxide contains M1=Cu, M2=Zn and M3=Al. In yet another aspect, a quaternary metal oxide contains M1=Cu, M2=Zn, M3=Al and M4=Zr.

In one embodiment, in the metal oxide, often M1 is Cu, M2 is Zn, and M3 is Zr, Al or Ce, wherein M3=Zr is preferred. Generally, the atomic percentage (atom-%) of M1 contained in the metal oxide comprised in the catalyst precursor is equal to or greater than 1, preferably equal to or greater than 4, and most preferably equal to or greater than 10. Generally, the atomic percentage (atom-%) of M1 contained in the metal oxide comprised in the catalyst precursor is equal to or less than 30, preferably equal to or less than 25, and most preferably equal to or less than 20. Generally, the atomic percentage (atom-%) of M2 contained in the metal oxide comprised in the catalyst precursor is equal to or greater than 1, preferably equal to or greater than 2, and most preferably equal to or greater than 3. Generally, the atomic percentage (atom-%) of M2 contained in the metal oxide comprised in the catalyst precursor is equal to or less than 15, preferably equal to or less than 14, and most preferably equal to or less than 13. Generally, the atomic percentage (atom-%) of M3, or, in the case of a ternary oxide, of (M3+M4), contained in the metal oxide comprised in the catalyst precursor is equal to or greater than 0.5, preferably equal to or greater than 1, and most preferably equal to or greater than 1.5. Generally, the atomic percentage (atom-%) of M3 or, in the case of a ternary oxide, of (M3+M4), contained in the metal oxide comprised in the catalyst precursor is equal to or less than 10, preferably equal to or less than 9, and most preferably equal to or less than 8. Generally, the atomic percentage (atom-%) of oxygen contained in the metal oxide comprised in the catalyst precursor is equal to or greater than 20, preferably equal to or greater than 25, and most preferably equal to or greater than 30. Generally, the atomic percentage (atom-%) of oxygen contained in the metal oxide comprised in the catalyst precursor is equal to or less than 80, preferably equal to or less than 78, and most preferably equal to or less than 76. The atomic percentage is suitably determined by EDX (Energy-dispersive X-ray spectroscopy) measurement.

In one embodiment, the preferred metal oxides comprised in the catalyst precursor are the systems $CuO/ZnO/ZrO_2$, $Cu/ZnO/ZrO_2$, $Cu/ZnO/Al_2O_3$, $Cu/ZnO/CeO_2$, $CuO/ZnO/Al_2O_3$, $CuO/ZnO/CeO_2$, $CuO/MgO/ZrO_2$ and $Cu/MgO/ZrO_2$, wherein metal oxide systems selected from the group consisting of $CuO/ZnO/ZrO_2$, $Cu/ZnO/ZrO_2$, $Cu/ZnO/Al_2O_3$ and $CuO/ZnO/Al_2O_3$ are especially preferred. In one aspect, the most preferred ternary metal oxide systems which are comprised in the catalyst are $CuO/ZnO/ZrO_2$ and $Cu/ZnO/ZrO_2$. In another embodiment, preferred quaternary oxide systems are oxides with the composition of $Cu^{2+}:Zn^{2+}:(Al^{3+}+Zr^{4+})=4.2:2:1$.

In one embodiment, the catalyst precursor comprising the metal oxide often is obtained by precipitation of a precipitate from at least one aqueous solution comprising at least one metal salt. In one aspect, an aqueous solution containing salts, preferably nitrate salts, of the metals contained in the catalyst precursor, is provided, and a basic aqueous solution is added to form a precipitate. In another aspect, two or more aqueous solutions containing one or more metals salts, preferably nitrates, are provided, and mixed simultaneously or subsequently with a basic aqueous solution. In one aspect, the two or more aqueous solutions containing one or more metals salts, preferably nitrates, are mixed, and the basic aqueous solution added. In another aspect, the one or mixture of two or more aqueous solutions of metal salt, are added to a basic aqueous solution, which is also denoted as the "reverse co-precipitation" method. The basic aqueous solution generally contains a basic metal salt, preferably a hydroxide, carbonate or bicarbonate of an alkaline or alkaline earth metal. A preferred basic salt is sodium carbonate. In a preferred aspect, metal salts, preferably nitrates, of M1, M2 and M3 or M1, M2, M3 and M4 are solved in water, and the basic aqueous solution, preferably sodium carbonate solution, is added. Generally, the one or more aqueous solutions to which the other one or more aqueous solutions are added are stirred. The addition speed generally depends on several factors, for example the reactor, temperature and concentration of the solutions involved. In one aspect, the addition speed at which the one or more aqueous solutions to which the other one or more aqueous solutions are added, is from 5 mL/h to 300 mL/h.; an addition speed of from 30 to 100 mL/h is preferred.

In one embodiment, the one or more aqueous solutions to which the other one or more aqueous solutions are added are kept in an ultrasound bath. In one embodiment, at least one salt of an organic acid, which is preferably selected from the group consisting of citrate and oxalate, is comprised in the one or more aqueous solutions during the precipitation step.

In a further embodiment, the reaction mixture in which the precipitate is formed usually is kept at a temperature of from 10 to 90° C. Generally, the temperature at which the reaction mixture in which the precipitate is formed is kept is equal to or higher than 10° C., preferably equal to or higher than 20° C., and most preferably equal to or higher than 30° C. Generally, the temperature at which the reaction mixture in which the precipitate is formed is kept is equal to or less than 90° C., preferably equal to or less than 85° C., and most preferably equal to or less than 80° C. A temperature of from 65 to 75° C. is preferred. Often, a pH of from 5.5 to 9, preferably of from 6.0 to 7, is kept while the one or more aqueous solutions is added to the other one or more aqueous solutions.

In one embodiment, after the addition of the one or more aqueous solutions to the other one or more aqueous solutions added, the reaction mixture usually is stirred at a given temperature and for a given time. This step is also denoted as "ageing". Usually, the reaction mixture is aged from 30 min to 36 hours. Often the ageing time is from equal to or more than 30 min, preferably equal to or more than 5 hours, even more preferably equal to or more than 10 hours, and most preferably equal to or more than 15 hours. Often the ageing time is from equal to or less than 36 hours, preferably equal to or less than 30 hours, even more preferably equal to or less than 25 hours, and most preferably equal to or less than 20 hours. Usually, the reaction mixture is aged at a temperature of from 10° C. to 90° C. Often the ageing temperature is from equal to or more than 10° C., preferably equal to or more than 20° C., even more preferably equal to or more than 25° C., and most preferably equal to or more than 30° C. Often the ageing temperature is from equal to or less than 90° C., preferably equal to or less than 85° C., even more preferably equal to or less than 80° C., and most preferably equal to or less than 75° C. In one aspect of the present invention, the reaction mixture is kept in an ultrasound bath during the ageing step. Usually, a pH of from 5 to 10, preferably of from 6.5 to 8, and most preferably of from 7.0 to 7.5 is kept in the reaction mixture during the ageing step. In one preferred aspect of this embodiment, when ageing is performed at a temperature of equal to or higher than 55° C., the ageing time generally is from equal to or more than 15 hours, preferably equal to or more than 16 hours, and most preferably equal to or more than 17 hours. In this aspect, the ageing time generally is from equal to or less than 36 hours, preferably equal to or less than 33 hours, and most preferably equal to or less than 30 hours. In another preferred aspect of the embodiment, when ageing is performed at a temperature of equal to or lower than 54.9° C., the ageing time generally is from equal to or more than 30 minutes, preferably equal to or more than 2 hours, and most preferably equal to or more than 3 hours. In this aspect, the ageing time generally is from equal to or less than 14.5 hours, preferably equal to or less than 12 hours, and most preferably equal to or less than 9 hours.

In one embodiment, which is preferred, the metal oxide precursor in the precipitate formed has a crystal structure which is essentially an aurichalcite and/or a malachite crystal structure. In this context, the term "malachite crystal structure" denotes a so-called "parent" structure of Cu2(CO3)(OH)2 (malachite), which sustains the uptake of other ions, such as Zn, Zr or additional Cu ions, into suitable metal positions within the parent structure. Also, the term "aurichalcite crystal structure" denotes a so-called "parent" structure of Zn3Cu2(OH)6(CO3)2 (aurichalcite), which sustains the uptake of other ions, such as Zn, Zr or additional Cu ions, into suitable metal positions within the parent structure. The term "crystal structure" also denotes the term "synthetic phase". Other synthetic phases can also be present in the precipitate as parent phases, for example Rosasit and Gerhardtit. The crystal structures are suitably determined by IR-spectroscopy or powder diffraction using X-ray.

Generally, after precipitation and optionally ageing, the precipitate is recovered from the aqueous phase of the reaction mixture by filtration or any other technique which is suited for a solid/liquid separation. The precipitate, from which the aqueous phase was separated, often is subsequently washed one or more times with water. Preferably, the water is distilled water. The water which is used for washing usually has a temperature from 10 to 100° C., preferably from 20° C. to 100° C.

Generally, the washed precipitate is dried at a temperature of from 80° C. to 120° C., preferably at a temperature of from 90° C. to 110° C. The precipitate is usually dried at the given temperature for from 12 to 36 hours, preferably from 14 to 30 hours.

In one embodiment, the precipitate is calcinated after recovery and optionally drying. "Calcinating" is intended to denote heating of the precipitate in an oxygen containing atmosphere, or, preferably, in an inert atmosphere, wherein an atmosphere consisting of or essentially consisting of N2 is most preferred. Calcination is usually carried out at a calcination temperature of from 200° C. to 450° C. The "calcination temperature" is intended to denote the temperature at which the precipitate is kept; usually, the calcination temperature is reached by a temperature ramp, which means that the calcination oven is heated at a certain heating rate until the calcination temperature is reached. Usually, the heating rate is from 50° C./h to 250°/h, preferably from 150° C./h to 220° C./h. Generally, the calcination temperature is from equal to or more than 200° C., preferably equal to or more than 240° C., even more preferably equal to or more than 280° C., and most preferably equal to or more than 290° C. Generally, the calcination temperature is from equal to or less than 450° C., preferably equal to or less than 420° C., even more preferably equal to or less than 390° C., and most preferably equal to or less than 370° C. The calcination time usually is from 1 to 6 hours. Generally, the calcination time is from equal to or more than 1 h, preferably equal to or more than 1.5, even more preferably equal to or more than 2 h, and most preferably equal to or more than 2.5 h. Generally, the calcination time is from equal to or less 6 h, preferably equal to or less than 5.5 h, even more preferably equal to or less than 5 h, and most preferably equal to or less than 4.5 h.

In one aspect, the calcination product is cooled actively, e.g. by using a gas stream, or inactively, by leaving to cool.

Generally, the calcination product is the catalyst precursor comprising a metal oxide and is usually used as such in the fluorination step using at least one gaseous fluorinating agent. In one aspect of the invention, the catalyst precursor and/or precipitate is treated prior to the subsequent steps with an aqueous solution containing fluoride anions, such as a NaF solution or by the addition of aqueous HF, with subsequent filtration and drying. In another aspect, an aqueous solution containing fluoride anions, such as a NaF solution, is present during the precipitation step. In yet another aspect of the invention, the catalyst precursor is subjected to at least one of the steps selected from crushing, pressing, grinding, milling and sieving. In addition, the catalyst precursor can in be mixed with other metal salts such as other metal oxides prior or after such physical treatment.

In one embodiment, in the process according to the present invention, the catalyst precursor obtained by precipitation, precipitate recovery and calcination, and optionally further physical treatment steps, consists of, or essentially consists of, metal oxide. "Essentially" intends to denote that the content of metal oxide in the catalyst precursor is equal to or higher than 70 wt %, preferably equal to or higher than 80 wt %, and most preferably equal to or higher than 90 wt %. Other compounds contained in the catalyst precursor can, for example, be metal salt hydrates, crystal water, metal hydroxides and/or metal carbonates. In yet another aspect of the invention, metal can be present in the catalyst precursor in oxidation state 0.

Generally, before the fluorination step, the catalyst precursor often has a BET (Brunner-Emmet-Teller) value of from 68 to 180 m2/g. Generally, the catalyst precursor has a BET value of equal to or greater than 68 m2/g, preferably of equal to or greater than 72 m2/g and most preferably of equal to or greater than 76 m2/g. Generally, the catalyst precursor has a BET value of equal to or less than 180 m2/g, preferably of equal to or less than 170 m2/g and most preferably of equal to or less than 160 m2/g. The BET (Brunner-Emmet-Teller) value is measured suitably by the method described by DIN ISO 9277, specifically by adsorption of nitrogen at 77 K in a Sorptomatic analyzer of the provider ThermoFisher.

The catalyst precursor is subjected to a fluorination step by applying at least one gaseous fluorination agents. In one embodiment, the at least one gaseous fluorination agent is selected from the group of elemental fluorine F2, HF, carbonyl fluoride and SF4. F2 and HF are preferred gaseous fluorination agents. Generally, the catalyst precursor is placed in a suitable reactor, such as a reactor made of or having a surface consisting of PFA (Perfluoroalkoxy alkane) or PTFE (polytetrafluoroethylene), or hastelloy or monel reactors which are resistant to corrosion by the at least one fluorination agent at the given fluorination conditions. The catalyst precursor usually is stirred during the fluorination reaction. Often, the reactor is evacuated for from 10 to 60 minutes, preferably for a time of from 20 to 40 minutes. In one embodiment, a fluorination agent pressure is regulated in the line supplying the at least one fluorination agent, which can be indicated as fluorination agent feed pressure. This pressure is also denoted as P1. Often, the reactor is then opened to the line supplying the at least one fluorination agent until an equilibrium fluorination pressure, also denoted as P2, is reached in the reactor. Generally, the reactor is then held at P2 for from 5 to 120 min fluorination reaction time. Generally, the fluorination time is equal to or greater than 5 min, preferably equal to or greater than 7 minutes, and most preferably from equal to or greater than 9 minutes. Generally, the fluorination reaction time is equal to or less than 120 min, preferably equal to or less than 60 minutes, and most preferably from equal to or less than 30 minutes. Generally, P1 is equal to or greater than 290 mbar, preferably equal to or greater than 300 mbar, and most preferably from equal to or greater than 310 mbar. Generally, P1 is equal to or less than 1550 mbar, preferably equal to or less than 1540 mbar, and more preferably from equal to or less than 1520 mbar. P1 values of from equal to or less than 1900 mbar are also suitable. Generally, P2 is equal to or greater than 90 mbar, preferably equal to or greater than 100 mbar, and most preferably from equal to or greater than 105 mbar. Generally, P2 is equal to or less than 700 mbar, preferably equal to or less than 680 mbar, and most preferably from equal to or less than 660 mbar.

Generally, the fluorination temperature is equal to or greater than 15° C., preferably equal to or greater than 18° C., and most preferably from equal to or greater than 20° C. Generally, the fluorination temperature is equal to or less than 30° C., preferably equal to or less than 28° C., and most preferably from equal to or less than 26° C. Fluorinating at room temperature, thus at temperatures of from 21° C. to 24° C., is most preferred. Depending on the catalyst precursor, fluorination time, fluorination temperature, P1 and P2, a certain amount of at least one fluorinating agent is consumed during the fluorination. Generally, the amount of the at least one fluorinating agent consumed in the fluorination step is equal to or greater than 0.1 mmol/g catalyst precursor, preferably equal to or greater than 0.2 mmol/g catalyst precursor, and most preferably equal to or greater than 0.3 mmol/g catalyst precursor. Generally, the amount of at least one fluorinating agent consumed in the fluorination step is equal to or less than 2 mmol/g catalyst precursor, preferably equal to or less than 1.9 mmol/g catalyst precursor, and most preferably equal to or less than 1.8 mmol/g catalyst precursor.

After the fluorination step, any remaining fluorinating agent is usually removed from the reactor by "rinsing" the reactor with gas, preferably an inert gas such as N2.

In one embodiment, at least one catalyst precursor according to the present invention is contained in a catalyst bed or a catalyst bed precursor. In this case, the fluorination with the at least one gaseous fluorinating agent is performed on the catalyst bed or catalyst bed precursor containing the catalyst precursor such that a catalyst bed, in particular a hydrogenation catalyst bed, containing a catalyst comprising a fluorinated metal oxide is formed.

The catalyst, in particular hydrogenation catalyst, comprising a fluorinated metal oxide often has a BET (Brunner-Emmet-Teller) value of from 30 to 150 m2/g. Generally, the catalyst comprising a fluorinated metal oxide has a BET value of equal to or greater than 30 m2/g, preferably of equal to or greater than 35 m2/g and most preferably of equal to or greater than 40 m2/g. Generally, the catalyst comprising a fluorinated metal oxide has a BET value of equal to or less than 150 m2/g, preferably of equal to or less than 140 m2/g and most preferably of equal to or less than 130 m2/g. The BET (Brunner-Emmet-Teller) value is measured suitably by the method described by DIN ISO 9277, specifically by adsorption of nitrogen at 77 K in a Sorptomatic analyzer of the provider ThermoFisher. If desired, the catalyst comprising a fluorinated metal oxide can be subjected to at least one of the steps selected from crushing, pressing, grinding, milling and sieving in order to achieve the optimal physical properties with regard to particle size. Generally, the atomic percentage (atom-%) of fluorine contained in the fluorinated metal oxide comprised in the catalyst, in particular hydrogenation catalyst, is equal to or greater than 1 atom-%, preferably equal to or greater than 2 atom-%, and most preferably equal to or greater than 3 atom-%. Generally, the atomic percentage (atom-%) of fluorine contained in the metal oxide comprised in the catalyst, in particular hydrogenation catalyst, is equal to or less than 50 atom-%, preferably equal to or less than 45 atom-%, and most preferably equal to or less than 40 atom-%. The atomic percentage is suitably determined by EDX (Energy-dispersive X-ray spectroscopy) measurement.

The catalyst, in particular hydrogenation catalyst, comprising a fluorinated metal oxide is also denoted by the term "catalyst comprising an oxidofluoridic compound".

In one aspect of the invention, the catalyst, in particular hydrogenation catalyst, comprising a fluorinated metal oxide can be pelletized, granulated or applied to a carrier material, for example by granulation on a rotary disc with water as auxiliary granulation additive.

In one aspect, the catalyst, in particular hydrogenation catalyst, comprising a fluorinated metal oxide obtained by the fluorination step is furnished with a layer of a layer of ionic liquid to obtain a "solid catalyst with Ionic Liquid Layer", also denoted as (SCILL) system. Principles of SCILL are described by U. Kernchen et al, Chem. Eng. Technol. 2007, 30, No. 8, 985-994, which is incorporated by reference. The catalyst comprising a fluorinated metal oxide is contacted with at least one suitable ionic liquid, preferably selected from the group consisting of [P6, 6, 6, 14][NTf2] (Trihexyltet-radecylphosphoniumbis(triflouromethylsulfonyl)imid), [N1, 1, 1, 8][PF](Trimethyloctyla-mmoniumtetra(nonafluoro-tert-butoxy)aluminat) and [BMIM][ES] (1-Methyl-3-butylimidazoliumethylsulfat). Preferably, the reaction is performed in the presence of a suitable organic solvent, for example halocarbons, preferably dichloromethane, or aromatic solvents such as toluene. Often, 1 g of hydrogenation catalyst is contacted with from 0.01 to 0.9 g, preferably from 0.1 to 0.3 g of ionic liquid. After removal of the solvent under reduced pressure, the catalyst comprising a fluorinated metal oxide layered with ionic liquid is obtained. The obtained SCILL catalyst comprising a fluorinated metal oxide can suitably be used for catalytic hydrogenation processes, in particular the catalytic hydrogenation of CO and/or CO2 to obtain methanol and/or dimethyl ether.

In one embodiment, the invention pertains further to a process for catalytic hydrogenation, wherein the hydrogenation catalyst is a catalyst comprising a fluorinated metal oxide. Preferably, the hydrogenation catalyst employed in the hydrogenation process was obtained by fluorination of a catalyst precursor comprising a metal oxide with at least one gaseous fluorination agent. In one aspect, the metal oxide is a ternary metal oxide, preferably the ternary metal oxide comprises Cu, most preferably the ternary metal oxide is CuO/ZnO/ZrO2. In another aspect, the hydrogenation catalyst comprising a fluorinated metal oxide is furnished with a layer of a layer of ionic liquid. Such a SCILL-catalyst is described above. All aspects concerning the catalyst, its characteristics and process details of how to obtain such a catalyst are described above.

In one embodiment, in the process for catalytic hydrogenation employing a hydrogenation catalyst, the hydrogenation catalyst is activated before the hydrogenation step. Often, in this step, at least part of at least one component of the fluorinated metal oxide, preferably CuO, is reduced to elemental metal, preferably Cu. The activation process is performed according to methods known to the person skilled in the art for non-fluorinated metal oxide catalysts, for example by heating the hydrogenation catalyst in a gas stream containing hydrogen at atmospheric or elevated pressure. In one aspect, the hydrogenation catalyst is activated in a gas stream containing hydrogen for from 30 to 120 minutes at from 180 to 350° C. In a preferred aspect, it is advantageous to submit the catalysts to a stepwise activation protocol. It has been found that the catalysts according to the present invention benefit from a step-wise activation protocol, in order to avoid exothermic temperature peaks which could enhance adverse processes such as sintering and diffusion. Often, an activation protocol comprises at least 2, preferably at least 4, and more preferably at least 7 steps is employed. In some aspects, 9 steps may be particularly advantageous. Generally, the activation steps are rising stepwise with respect to temperature and often show a gradual increase in gas dosage. Often, the temperature of the first activation step is from 80 to 120° C., while the temperature of the final activation step is from 180 to 280° C. Generally, the initial hydrogen content in the gas stream in the first activation step is from 8 to 15 vol %, and increases stepwise until the gas stream consists or essentially consists of hydrogen in the last activation step. Often, the initial pressure in the first activation step is from 3 to 6 bar, and increases stepwise until a pressure of from 35 to 45 bar in the last activation step.

In one embodiment, the preferred hydrogenation process wherein the activated catalyst is employed, is the hydrogenation of CO2 and/or CO to obtain methanol and/or dimethyl ether. Most preferred is the hydrogenation of CO2 to obtain methanol. In one aspect, the catalytic hydrogenation of CO2 employing the activated hydrogenation catalyst according to the present invention is usually performed at a pressure of from 20 to 60 bar, preferably 25 to 55 bar, and most preferably of from 30 to 50 bar. In one aspect, the temperature of the hydrogenation process is usually selected from 130 to 270° C. Generally, the temperature of the hydrogenation process is equal to or greater than 130° C., preferably equal to or greater than 140° C. and most preferably equal to or greater than 150° C. Generally, the temperature of the hydrogenation process is equal to or less than 270° C., preferably equal to or less than 260° C. and most preferably equal to or less than 250° C. Generally, a gas mixture comprising hydrogen gas and the hydrogenation target (HT) is fed to the hydrogenation process. Preferably the hydrogenation target is CO2. In a preferred aspect, no other gas is present in the gas mixture which is fed to the hydrogenation process, but hydrogen and the hydrogenation target. Generally, the ratio of hydrogen to HT is from 1:5 to 5:1. Preferably, the ratio is from 3:1 to 1:3. The gas hourly space velocity (GHSV) during the hydrogenation reaction, preferably when the hydrogenation target is CO2, is from 3000 to 20000, preferably from 3100 to 17000 and most preferably from 3200 to 14000 Nml g(Kat)$^{-1}$h$^{-1}$. The hydrogenation is suitably performed in a tube reactor, but other reactors suitable for hydrogenation processes can also be used. In one aspect, at least one other gas G1, preferably N2, is present in the gas mixture which is fed to the hydrogenation process. Usually, the at least one other gas G1 is present in a ratio of G1:(H2+HT) of from 0.05:9.95 to 9.95:0.05, preferably from 0.05:9.95 to 0.1:9.9.

In one embodiment, the hydrogenation process according to the present invention can be conducted batch wise or continuously, wherein continuously is preferred.

The examples which follow are intended to illustrate the present invention without, however, limiting the scope thereof.

EXPERIMENTS

Experiment 1

Synthesis of a Catalyst Precursor Comprising a Ternary Metal Oxide (Compound A and B)

1000 mL H2O were stirred in a reactor. The water was heated to 70° C. The water was stirred and an aqueous solution containing Cu(NO3)2.3 H2O (45.66 g, 188.8 mmol, 4.2 eq.), Zn(NO3)2.6 H2O (26.35 g, 88.8 mmol, 2 eq.) und ZrO(NO3)2.7 H2O (15.32 g, 44.8 mmol, 1 eq.) in H2O (320 ml) and an basic aqueous solution Na2CO3 (33.6 g, 316.8 mmol, 7.1 eq.) in H2O (320 ml) was added simultaneously at a rate of 60 mL/h. The reaction mixture was kept at 70° C. and pH 7. After completed addition, the reaction mixture was kept at 50° C. for 18 hours. The light green precipitate was separated by filtration, washed with water (4×500 mL) and dried overnight at 105° C. The dried solid was heated at a rate of 200° C./h in a nitrogen gas atmosphere until the calcination temperature of 300° C. was reached, then calcinated at 2.5 hours at 300° C. Compound A and B consist essentially of Cu/ZnO/ZrO2.

TABLE 1

Properties of Catalyst Precursors A and B

| | Cu [atom %] | Zn [atom %] | Zr [atom %] | O [atom %] | F [atom %] | BET [m2/g] |
|---|---|---|---|---|---|---|
| Compound A | 19 | 9 | 4 | 68 | 0 | 81.1 |
| Compound B | 17 | 8 | 4 | 71 | 0 | 113.7 |

Experiment 2

Fluorination of Compound A or B with F2 or HF

Component A or B was placed in a PFA reactor (volume 130 mL) and the reactor was evacuated for 30 minutes. Fluorine pressure P1 was regulated in the Monel line to the reactor. The valve between reactor and Monel line was opened, and the reactor was relaxed until the equilibrium pressure P2 was reached. P2 was held for 15 minutes (if fluorination agent was F2) or 30 minutes (if fluorinating agent was HF) at room temperature. After the reaction time, the reactor was rinsed with N2 and the fluorinated compounds C—H were obtained black solid compounds.

Reaction conditions are displayed in Table 2

TABLE 2

Reaction conditions for fluorinated compounds C—H synthesis

| | Product | | | | | |
|---|---|---|---|---|---|---|
| | Product C | Product D | Product E | Product F | Product G | Product G |
| Mass [g] | 1.5 | 1.00 | 2.01 | 2.04 | 1.5 | 1.51 |
| precursor | B | B | A | A | B | B |
| P1 [mbar] | 362 | 950 | 313 | 461 | 910 | 1400 |
| P2 [mbar] | 93 | 297 | 110 | 141 | 180 | 290 |
| fluorinating agent consumed [mmol/g] | 0.5 | 1.8 | 0.5 | 0.8 | 0.7 | 1.1 |
| (fluorinating agent) | F2 | F2 | F2 | F2 | HF | HF |

Table 3 displays the product characteristics.

TABLE 3

Product characteristics of compounds C—H

| Compound | Cu [atom %] | Zn [atom %] | Zr [atom %] | O [atom %] | F [atom %] | BET [m2/g] |
|---|---|---|---|---|---|---|
| C | 21 | 9 | 5 | 59 | 6 | 102.8 |
| D | 22 | 10 | 4 | 57 | 7 | 85.1 |
| E | 25 | 12 | 4 | 51 | 8 | 66.2 |
| F | 23 | 11 | 4 | 53 | 9 | 68.7 |
| G | 19 | 10 | 4 | 60 | 7 | 83.4 |
| H | 17 | 8 | 4 | 57 | 14 | 60.5 |

Experiment 3

Hydrogenation Experiments

Compounds C—H were activated in a hydrogen atmosphere at elevated temperatures.

The activated compounds C—H were placed in a tube reactor, and the activities in a hydrogenation process at 40 bar pressure, 240° C. and a GHSV of about 4000 Nml g(Kat)$^{-1}$h$^{-}$. The feed gas had a composition of about 3:1 (H2:CO2). Table 4 displays the hydrogenation experiment conditions and results.

TABLE 4

Hydrogenation experiment conditions and results

| Experiment # | compound | Mass cat [g] | F [atom %] | activity [mmol g (Kat)$^{-1}$ h$^{-1}$] | Increase of activity [%] | CO2 turnover [%] |
|---|---|---|---|---|---|---|
| 3a | A | 1.071 | 0 | 4.4 | — | 9 |
| 3b | B | 0.871 | 0 | 5.7 | — | 12 |
| 3c | C | 1.026 | 6 | 7.2 | 27 | 15 |
| 3d | D | 0.841 | 7 | 9.0 | 58 | 19 |
| 3e | E | 1.012 | 8 | 4.3 | 68 | 9 |
| 3f | F | 0.995 | 9 | 4.9 | 91 | 10 |
| 3g | G | 0.903 | 7 | 7.0 | 23 | 13 |
| 3h | H | 1.001 | 14 | 6.6 | 17 | 14 |

The invention claimed is:

1. A hydrogenation catalyst comprising a fluorinated metal oxide, wherein an atomic percentage of fluorine (F) contained in the fluorinated metal oxide is equal to or greater than 3 atom %, and
wherein the fluorinated metal oxide is a fluorinated ternary metal oxide consisting essentially of Cu, Zn, Zr, O, and F.

2. The hydrogenation catalyst according to claim 1, wherein the fluorinated ternary metal oxide has a BET (Brunner-Emmet-Teller) value from 30 to 150 m$^2$/g.

3. The hydrogenation catalyst according to claim 2, wherein the BET (Brunner-Emmet-Teller) value is at least about 40 m$^2$/g and equal to or less than 130 m$^2$/g.

4. The hydrogenation catalyst according to claim 1, wherein the atomic percentage is in a range from 6 atom % to 14 atom %.

5. The hydrogenation catalyst according to claim 1, wherein the fluorinated ternary metal oxide comprises a metal oxide system selected from the group consisting of: Cu/ZnO/ZrO$_2$ and CuO/ZnO/ZrO$_2$.

6. The hydrogenation catalyst according to claim 5, wherein the metal oxide system is CuO/ZnO/ZrO$_2$.

7. The hydrogenation catalyst according to claim 1 further comprising a layer of ionic liquid.

8. A hydrogenation catalyst comprising a fluorinated metal oxide, wherein an atomic percentage of fluorine contained in the fluorinated metal oxide is equal to or greater than 3 atom %, and further comprising a layer of ionic liquid.

* * * * *